United States Patent
Saffar et al.

(10) Patent No.: US 9,468,533 B2
(45) Date of Patent: Oct. 18, 2016

(54) METHOD OF RECONSTRUCTING A PATIENT'S WRIST

(71) Applicant: TriMed, Inc., Santa Clarita, CA (US)

(72) Inventors: Philippe Saffar, Neuilly-sur-Seine (FR); Anders Hakansson, Malmo (SE)

(73) Assignee: TriMed, Inc., Santa Clarita, CA (US)

( * ) Notice: Subject to any disclaimer, the term of this patent is extended or adjusted under 35 U.S.C. 154(b) by 0 days.

(21) Appl. No.: 14/289,140

(22) Filed: May 28, 2014

(65) Prior Publication Data

US 2014/0358243 A1 Dec. 4, 2014

Related U.S. Application Data

(60) Provisional application No. 61/828,933, filed on May 30, 2013.

(51) Int. Cl.
*A61F 2/42* (2006.01)
*A61F 2/30* (2006.01)

(52) U.S. Cl.
CPC .... *A61F 2/4261* (2013.01); *A61F 2002/30131* (2013.01); *A61F 2002/30327* (2013.01); *A61F 2002/30578* (2013.01); *A61F 2002/30622* (2013.01); *A61F 2002/30772* (2013.01); *A61F 2002/30934* (2013.01); *A61F 2002/4264* (2013.01)

(58) Field of Classification Search
CPC .................................................. A61F 2/4261
See application file for complete search history.

(56) References Cited

U.S. PATENT DOCUMENTS

| | | | | |
|---|---|---|---|---|
| 5,702,470 A | * | 12/1997 | Menon | A61B 17/15 623/21.12 |
| 6,383,223 B1 | * | 5/2002 | Baehler | A61F 2/4241 623/16.11 |
| 2007/0185582 A1 | * | 8/2007 | Palmer | A61F 2/4261 623/21.12 |
| 2010/0010636 A1 | * | 1/2010 | Shultz | A61F 2/4261 623/21.12 |

* cited by examiner

*Primary Examiner* — Yashita Sharma
*Assistant Examiner* — Daniel Bissing
(74) *Attorney, Agent, or Firm* — Wood, Phillips, Katz, Clark & Mortimer (57) ABSTRACT

A method of reconstructing a patient's wrist. A prosthesis is provided having proximal and distal assemblies. The distal assembly has a body with a U-shaped portion. The proximal and distal assemblies have surfaces that cooperate to guide movement between the proximal and distal assemblies. The proximal assembly is fixed to the patient's radius. The hand is prepared for placement of the distal assembly by removing cartilage against a plurality of carpal bones without significantly altering the configuration of stable volume of at least one of the patient's carpal bones in the first carpal row. The U-shaped portion of the body is placed against a plurality of bones in the first carpal row. Separate locations on the body are secured to a plurality of carpal bones.

24 Claims, 9 Drawing Sheets

METHOD OF RECONSTRUCTING A PATIENT'S WRIST

CROSS-REFERENCE TO RELATED APPLICATIONS

This is a non-provisional patent application claiming priority to U.S. Provisional Ser. No. 61/828,933, filed May 30, 2013, entitled "Wrist Prosthesis", which is hereby incorporated by reference in its entirety.

BACKGROUND OF THE INVENTION

1. Field of the Invention

This invention relates to wrist reconstruction and, more particularly, to a method of reconstructing a patient's wrist utilizing a prosthesis with cooperating proximal and distal assemblies.

2. Background Art

Wrist reconstruction is commonly performed to repair the wrist region that may be damaged due to degenerative arthritis and/or from a specific injury. Injuries and/or arthritis may compromise the small carpal bones that make up the wrist, the radius, and/or the ulna. Cartilage is located between the carpal bones and, when intact, guides generally pain-free movement between the carpal bones as an individual moves his/her wrist through various distinct motions. Deterioration of this cartilage may result in direct bone-on-bone contact, which can cause pain severe enough to warrant reconstructive surgery involving the use of a prosthesis.

There are a great number of complications associated with existing wrist prostheses. These complications are due mainly to the conventional manner of fixation of a distal assembly at the carpal region. Typically, a large carpal bone resection is performed and a distal component is inserted with a distal fixation made by two or three screws or prongs in the residual carpus and metacarpus.

Figure 1:
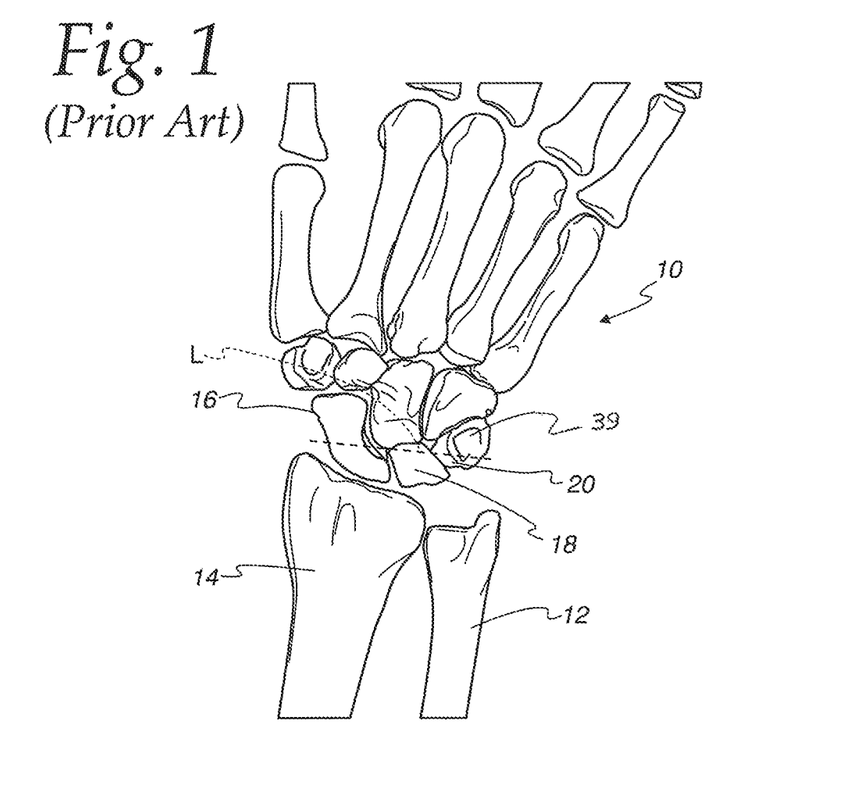
FIG. 1 is a fragmentary view of the bone structure of a patient's hand and arm and showing a conventional resection location for carpal bones on the hand to accommodate an assembly on a prosthesis.

In FIG. 1 an exemplary, conventional resection is depicted on a hand 10 shown in relationship to a portion of an individual's ulna 12 and radius 14. A significant portion of the first carpal row (including scaphoid, lunate and triquetrum carpal bones) is resected, with a separation border indicated by the line L. This resection normally involves the removal of a substantial portion of a stable volume of the scaphoid carpal bone 16, the lunate carpal bone 18, and the triquetrum carpal bone 20.

The distal assembly fixed to the remaining portion of the resected bone region is subjected to distraction forces when strains are produced on the hands and to rotational forces, with there being a resulting possibility of loosening of the screws and/or breakage of the bones where the screws are inserted. These prostheses are used primarily for patients with rheumatoid arthritis and rarely post-traumatic wrist destruction from osteoarthritis.

Existing wrist prostheses generally have a common design with a distal fixation on the carpus and metacarpus using different types of screws and prongs fixed in a direction longitudinally, i.e., generally parallel to the length of the individual's radius. They all share a great deal of complication due to this fixation because of the distracting forces applied to the component, among which are: breakage of the prosthesis; fracture of the metacarpal; loosening of the screws; etc.

Further, since a significant stable volume of the carpal bones is removed to accommodate the prosthesis, in the event that the prosthesis fails, a very difficult arthrodesis may become necessary.

The industry continues to seek prostheses that are durable and long-lasting, and which do not require any substantial reconfiguration of the stable existing bone structure that might complicate follow-up procedures in which partial or full reconstruction take place.

SUMMARY OF THE INVENTION

In one form, the invention is directed to a method of reconstructing a patient's wrist to facilitate movement between the patient's hand and radius. The method includes the steps of: providing a prosthesis made up of proximal and distal assemblies, wherein the distal assembly has a body with a U-shaped portion, and wherein the proximal and distal assemblies have surfaces that are configured to cooperate with each other to guide movement between the proximal and distal assemblies; fixing the proximal assembly to the patient's radius; preparing the hand for placement of the distal assembly by removing cartilage against a plurality of the patient's carpal bones without significantly altering the configuration of stable volume of at least one of the patient's carpal bones in the patient's first carpal row; after preparing the hand for placement of the distal assembly, placing the U-shaped portion of the body against a plurality of carpal bones in the patient's first carpal row; and with the U-shaped portion of the body placed against the carpal bones in the patient's first carpal row, securing separate locations on the body to a plurality of the patient's carpal bones.

In one form, the step of removing cartilage involves removing cartilage against the patient's scaphoid and lunate carpal bones so that the U-shaped portion of the body can be placed directly against a part of each of the scaphoid and lunate carpal bones.

In one form, the step of removing cartilage involves removing cartilage from between the patient's lunate carpal bone and each of the scaphoid and capitate carpal bones.

In one form, the U-shaped portion of the secured body extends to against the patient's triquetrum carpal bone.

In one form, the step of removing cartilage involves removing cartilage against the triquetrum carpal bone so that the U-shaped portion of the body can be placed directly against a part of the triquetrum carpal bone.

In one form, the step of removing cartilage involves removing cartilage from between the triquetrum carpal bone and the patient's hamate carpal bone.

In one form, the method of reconstructing a patient's wrist further includes the step of fusing a plurality of the patient's carpal bones together.

In one form, the step of fusing a plurality of the patient's carpal bones together is effected through the step of securing the body to a plurality of the patient's carpal bones.

In one form, the step of securing the body to a plurality of the patient's carpal bones involves directing a plurality of fasteners into a plurality of the patient's carpal bones.

In one form, the step of directing a plurality of fasteners into a plurality of the patient's carpal bones involves directing one of the plurality of fasteners through the body and one of the patient's carpal bones and into another one of the patient's carpal bones.

In one form, the step of directing a plurality of fasteners into a plurality of the patient's carpal bones involves directing: a) a first fastener in a first direction through the body and into one of the patient's carpal bones along a first line that is transverse to a reference line that extends generally parallel to a length of the patient's radius; and b) a second fastener in a second direction through the body and into one of the patient's carpal bones along a second line that is transverse to the reference line. The first and second directions are generally opposite to each other.

In one form, the first fastener is directed through the patient's triquetrum carpal bone and into the patient's hamate carpal bone.

In one form, the second fastener is directed through the patient's scaphoid carpal bone and into the patient's capitate carpal bone.

In one form, the body has an overall "U" shape with an elongate base having a length and extending into spaced legs. The elongate base has oppositely facing first and second U-shaped surfaces. The first U-shaped surface opens towards the patient's hand and contacts a plurality of the patient's carpal bones with the body secured to the patient's carpal bones. The "U" of the second U-shaped surface opens in the same direction as the first U-shaped surface and defines a guide surface that engages a guide surface on the proximal assembly to guide relative movement between the proximal and distal assemblies.

In one form, the guide surface on the body is convex in shape with the body viewed from a cross-sectional perspective taken transversely to the length of the elongate base. The guide surface on the proximal assembly is concave in shape as viewed in cross section corresponding to the cross-sectional perspective for the body.

In one form, the convex and concave shapes are approximated by arcs of circles with first and second radii respectively. The second radius is greater than the first radius.

In one form, the step of providing a prosthesis involves providing a prosthesis wherein the proximal and distal assemblies are configured to guide relative movement of the patient's hand relative to the patient's radius about a line that extends generally parallel to a length of the patient's radius.

In one form, the proximal and distal assemblies are configured to guide relative movement of the patient's hand relative to the patient's radius around the line through a controlled range on the order of at least 20°.

In one form, the proximal and distal assemblies have control surfaces that abut to limit relative turning of the distal assembly in opposite directions relative to the proximal assembly around a line that extends generally parallel to a length of the patient's radius. The control surfaces are configured so that the distal assembly can turn around the line relative to the proximal assembly through a range of at least 10°.

In one form, the body has an opening in the base and an opening in each of the spaced legs, each to accept a fastener. The legs extend in substantially parallel relationship to each other.

In one form, the body has an overall "U" shape with a U-shaped surface which engages a U-shaped surface on the proximal assembly. The U-shaped surfaces are each approximated by an arc with a radius centered on a line substantially perpendicular to a plane bisecting the patient's fingers in a flattened state. The radius of the arc approximating the U-shaped surface on the proximal assembly is greater than the radius of the arc approximating the U-shaped surface on the body.

DETAILED DESCRIPTION OF THE PREFERRED EMBODIMENT

Figure 2:
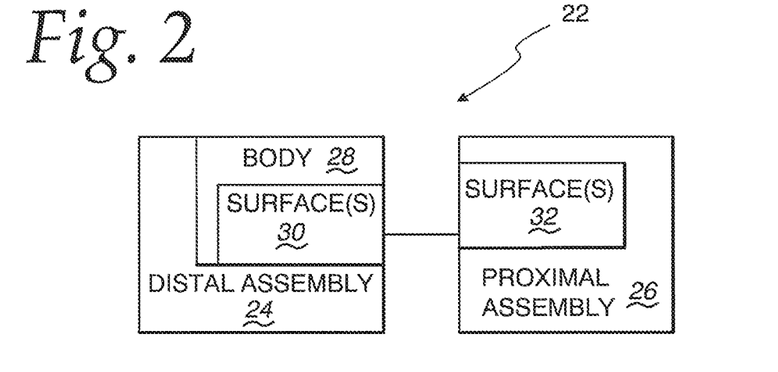
FIG. 2 is a schematic representation of a prosthesis, according to the present invention, and including cooperating proximal and distal assemblies.

FIG. 2 is a schematic representation of a prosthesis at 22, according to the present invention. The schematic showing of the prosthesis 22 is intended to encompass the specific forms hereinbelow described, as well as ones with variations of the basic components and their interaction as would be apparent to one skilled in the art based upon the teachings herein.

The prosthesis 22 consists of a distal assembly 24 attached to a patient's hand 10 and a cooperating proximal assembly 26 attached to a patient's arm/radius 14. The distal assembly 24 has a body 28 with at least one surface 30 that cooperates with at least one surface 32 on the proximal assembly 26 to controllably guide relative movement between the patient's hand 10 and radius 14.

As noted above, the parts generically identified in FIG. 2 may take a form as shown herein or may be modified in virtually an unlimited number of ways to perform a method consistent with the teachings herein.

Figure 3:
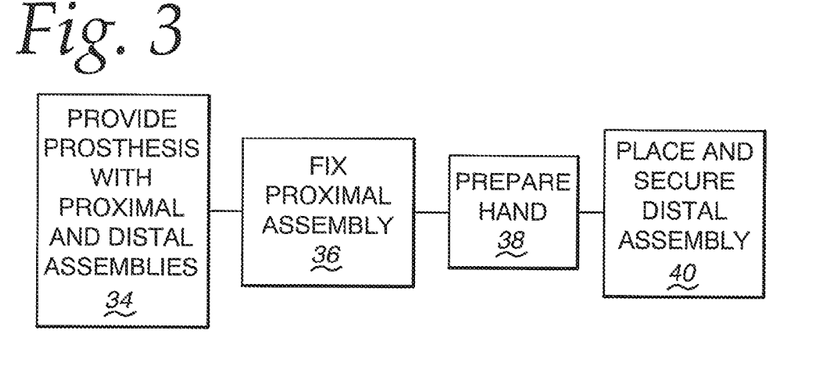
FIG. 3 is a flow diagram representation of a method of reconstructing a patient's wrist, according to the present invention.

With the prosthesis 22, a method of reconstructing a patient's wrist, to facilitate movement between the patient's hand 10 and radius 14, can be carried out as shown in flow diagram form in FIG. 3.

As shown at block 34, a prosthesis is provided as represented in FIG. 2.

As shown at block 36, the proximal assembly is fixed to the patient's radius.

As shown at block 38, the patient's hand is prepared for placement of the distal assembly by removing cartilage against a plurality of carpal bones without significantly altering the configuration of the stable volume of at least one of the carpal bones in the patient's first carpal/proximal row—namely the scaphoid, lunate, and triquetrum bones 16, 18, 20, successively. The cartilage of the pisiform carpal bone 39 is preferably left intact. Preferably, the stable volume of at least one of the patient's scaphoid and lunate carpal bones is kept substantially intact. Ideally, the stable volume of all the carpal bones in the first carpal row is retained intact.

After preparing the hand, and as shown at block 40, a U-shaped portion of the body on the distal assembly is placed against at least the scaphoid and lunate carpal bones and secured to a plurality of the patient's carpal bones.

With the proximal and distal assemblies operatively situated on the patient, the cooperating surfaces on the proximal and distal assemblies guide multi-dimensional movement between the proximal and distal assemblies in a controlled manner intended to simulate natural wrist motion.

Details of one exemplary form of prosthesis 22 will now be described with respect to FIGS. 3-19.

The distal assembly 24 has at least a portion that is U-shaped. In a preferred embodiment, substantially the entire body 28 is U-shaped, consisting of an elongate base 42 having a length, as indicated by the double-headed arrow L, and extending into spaced legs 44, 46 which project in substantially parallel lines.

The body 28 has oppositely facing first and second U-shaped surfaces 48, 30, respectively. The first U-shaped surface 48 faces the patient's hand 10 with the body 28 secured to the patient's hand 10. The first U-shaped surface 48 on the body 28 is secured against certain of the patient's carpal bones. As seen in FIGS. 15-18, the U-shaped surface 48 is configured to nominally match the contour of, and extend over, a plurality of carpal bones; namely the scaphoid carpal bone 16, the lunate carpal bone 18, and the triquetrum carpal bone 20 which together make up the first carpal row.

Figure 14:
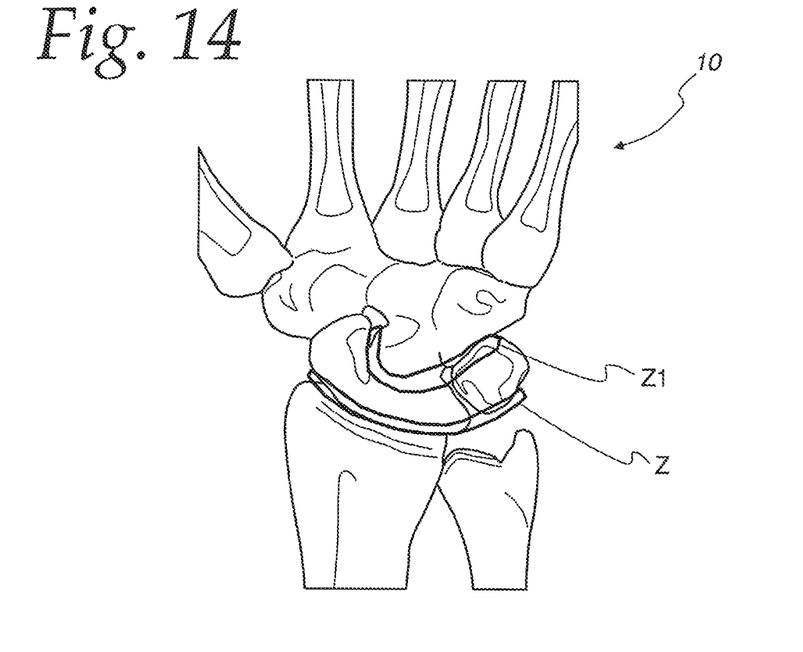
FIG. 14 is a view as in FIG. 1 and showing zones where cartilage is removed from against carpal bones as part of the inventive method.
Figure 15:
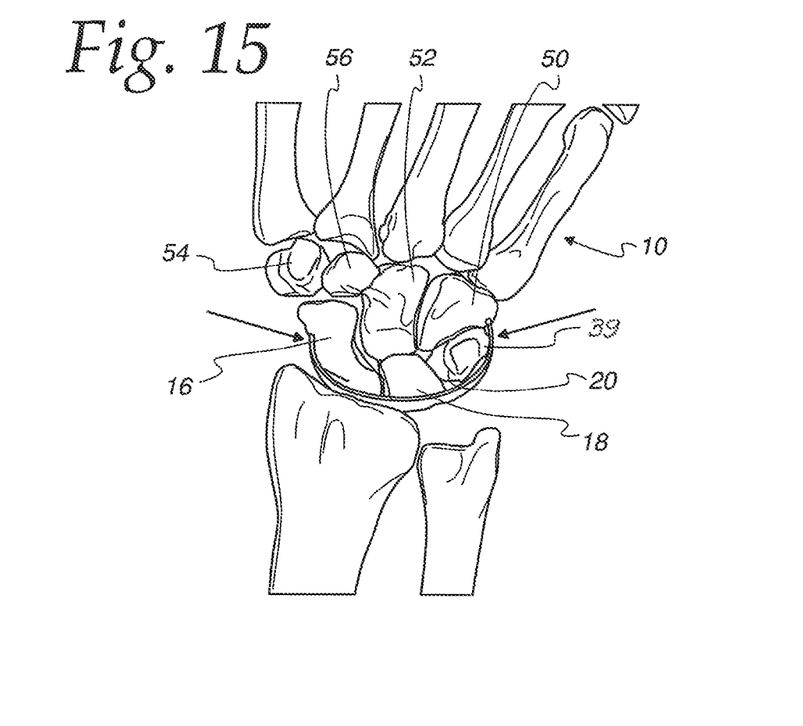
FIG. 15 is a view as in FIG. 14 and showing the distal assembly operatively positioned.
Figure 16:
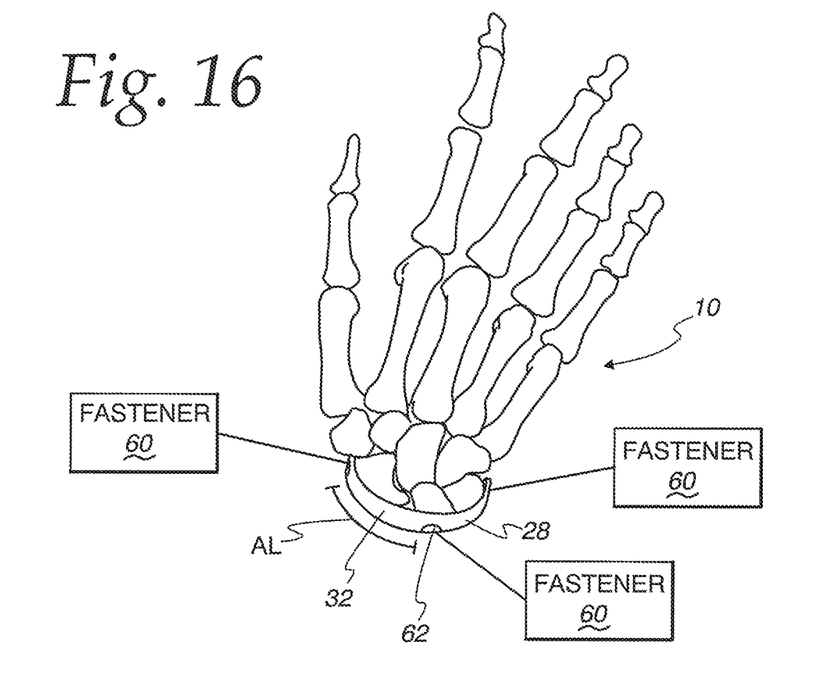
FIG. 16 is a view as in FIG. 15 and showing the distal assembly and carpal bones moved to a different angle relative to the metacarpus region.

As part of the step of preparing the hand for placement of the distal assembly 24, cartilage against the carpal bones in the first carpal row in the zone Z, identified in FIG. 14, is removed, thereby to allow direct contact between the first U-shaped surface 48 on the body 28 and a plurality, or all, of the carpal bones in the first carpal row. As noted above, the cartilage of the pisiform carpal bone 39 is preferably left intact so that there is no direct contact between the body 28 and pisiform carpal bone 39.

While some bone material may be removed from the carpal bones in the first carpal row during the preparation step, it is contemplated that the configuration of the stable volumes of the carpal bones is not significantly altered during this process. As a result, the carpal bones in the first carpal row, that are not compromised by arthritis, or injury, etc., remain significantly intact, whereby they might be utilized in a subsequent procedure to replace or reconstruct the distal assembly 24 on the prosthesis 22.

Additional cartilage on and between carpal bones is removed in the zone identified as Z1 in FIG. 14. As a result, direct bone-on-bone contact is permitted between: a) the triquetrum carpal bone 20 and hamate carpal bone 50; b) the lunate carpal bone 18 and capitate carpal bone 52; and c) the scaphoid carpal bone 16 and capitate carpal bone 52. Additional cartilage may be removed from against carpal bones in the first carpal row, and those making up the distal carpal row—namely, the capitate and hamate carpal bones 52, 50, successively.

Preferably, the carpal bones are fused where there is direct bone-on-bone contact, preferably including an arthrodesis of the midcarpal joint between the first and second rows (capitate and hamate). This fusion may be effected separately as by the use of grafting material and/or additional structural components. More preferably, the fusion is effected through fasteners 60 extending in three separate lines L1, L2, L3, as identified in FIG. 17, used to secure the body 28. The fasteners 60 may take any conventional form and will typically be threaded fasteners with heads that seat in undercuts 62 so as not to project appreciably from the surface contour of the body 28.

Figure 17:
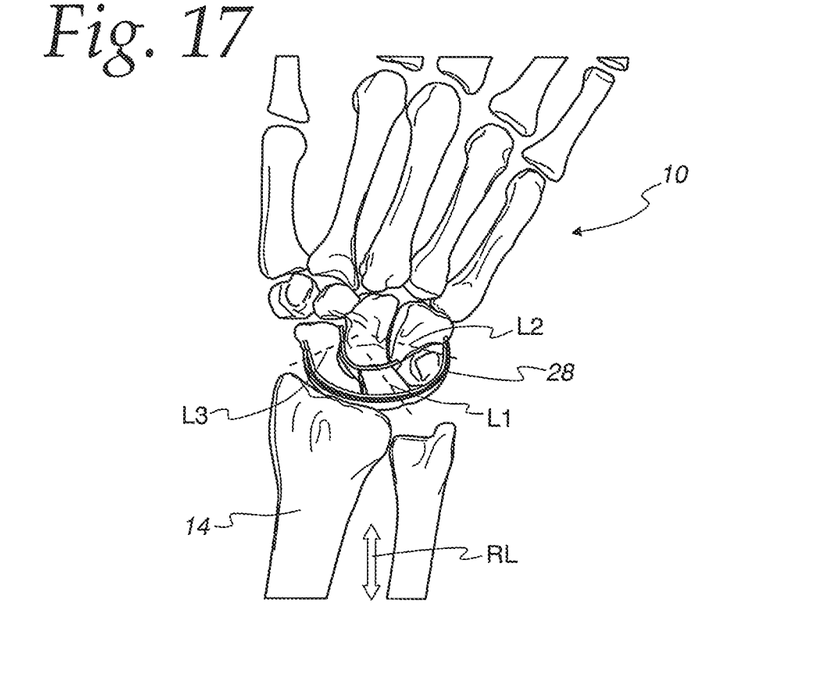
FIG. 17 is a view as in FIG. 15 and showing locations for fasteners to secure the distal assembly.

A fastener 60 extending in the line L1 is directed through the lunate carpal bone 18 and into the capitate carpal bone 52. The fastener 60 extending along the line L2 extends through the hamate carpal bone 50 and into the capitate carpal bone 52. The fastener 60 extending in the line L3 extends through the scaphoid carpal bone 16 and into the capitate carpal bone 52.

By removing the cartilage, as described above, the carpal bone fusion is facilitated. Further, the bone-on-bone contact affords greater stability. Still further, the removed cartilage creates a space approximately equaling that required for the body 28 so that the total dimension of the hand and wrist, including the body 28, between the fingertips and radius 14 is not substantially changed.

The second U-shaped surface 30 is configured to cooperate with the surface 32 on the proximal assembly 26 in a manner as described in detail below. The "U" of the second surface 30 opens in the same direction, i.e., towards the patient's hand 10, as the first U-shaped surface 48.

Figure 6:
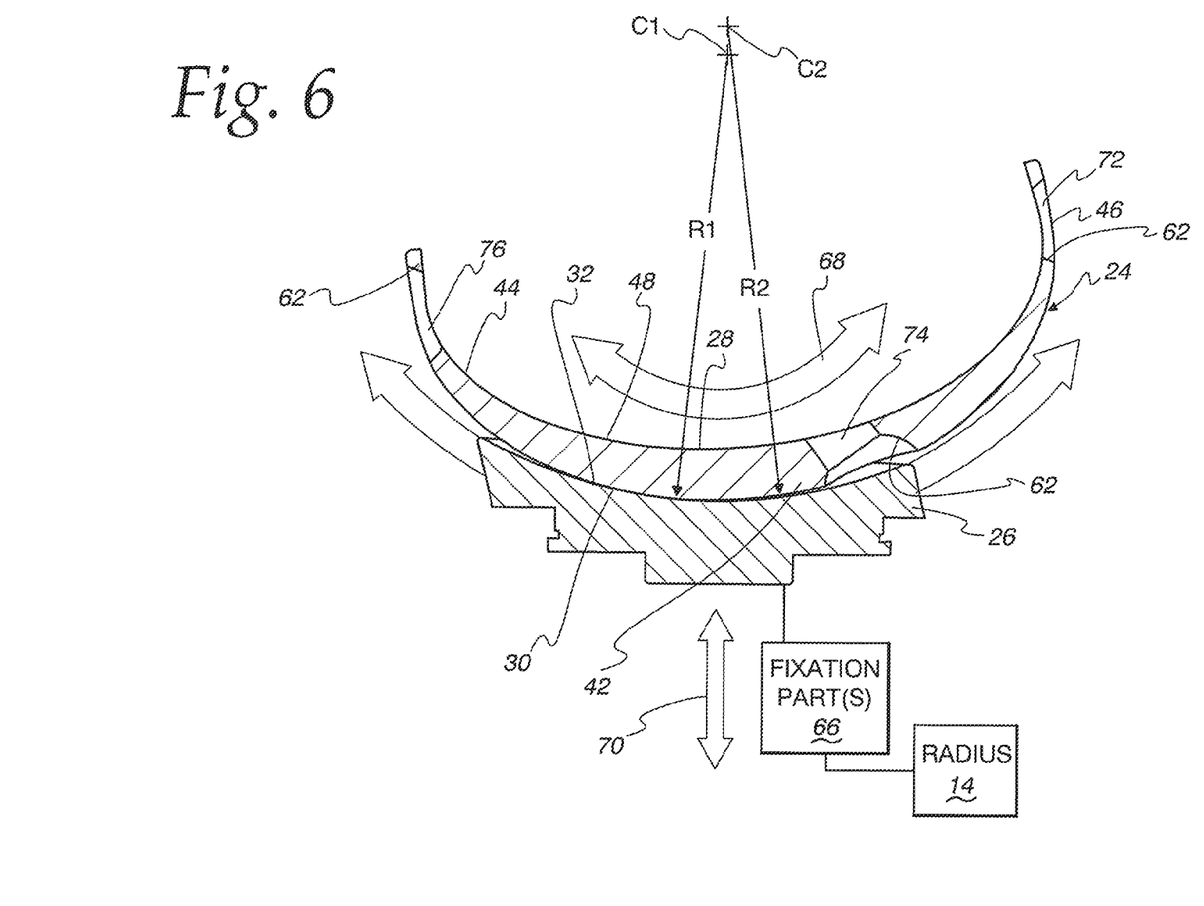
FIG. 6 is an enlarged, cross-sectional view of the prosthesis taken along line 6-6 of FIG. 4.
Figure 7:
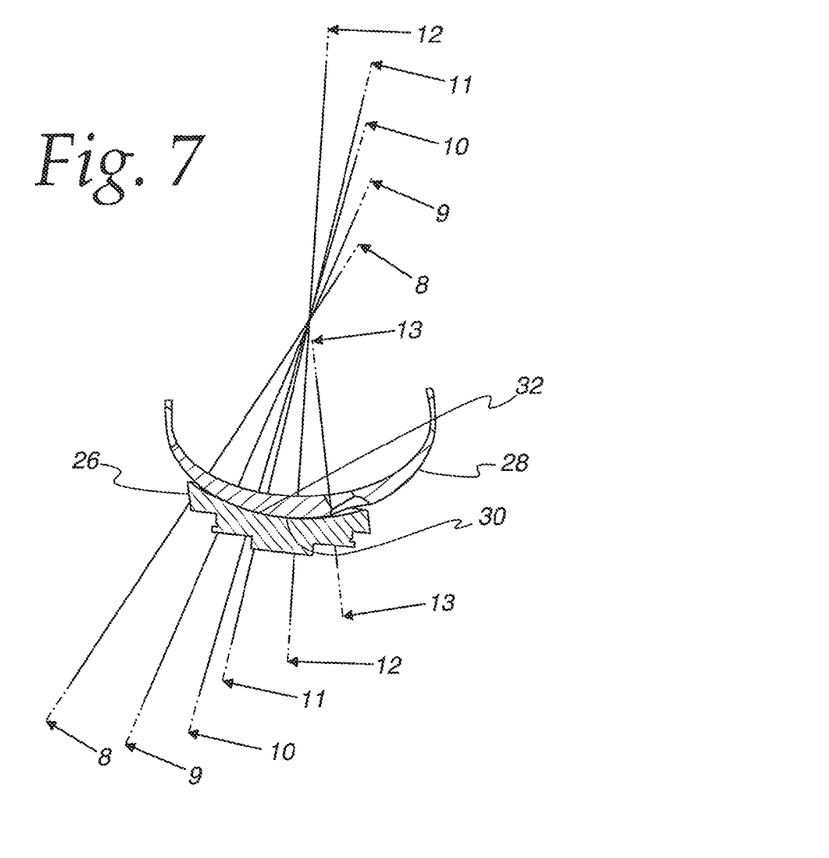
FIG. 7 is a reduced view as in FIG. 6 and identifying different locations from which cross-sectional views, described below, are taken.
Figure 8:
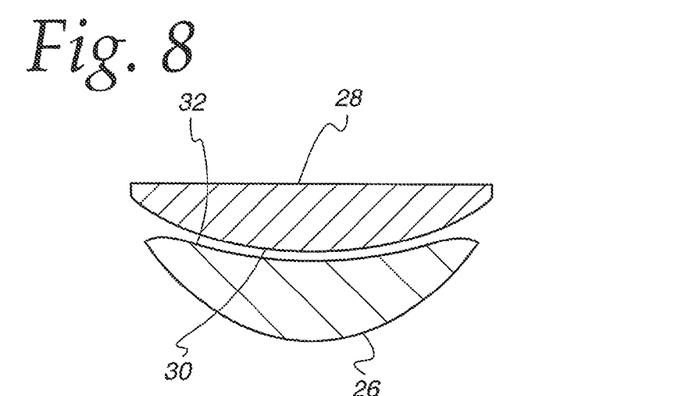
FIG. 8 is an enlarged, cross-sectional view of the prosthesis taken along line 8-8 of FIG. 7.
Figure 9:
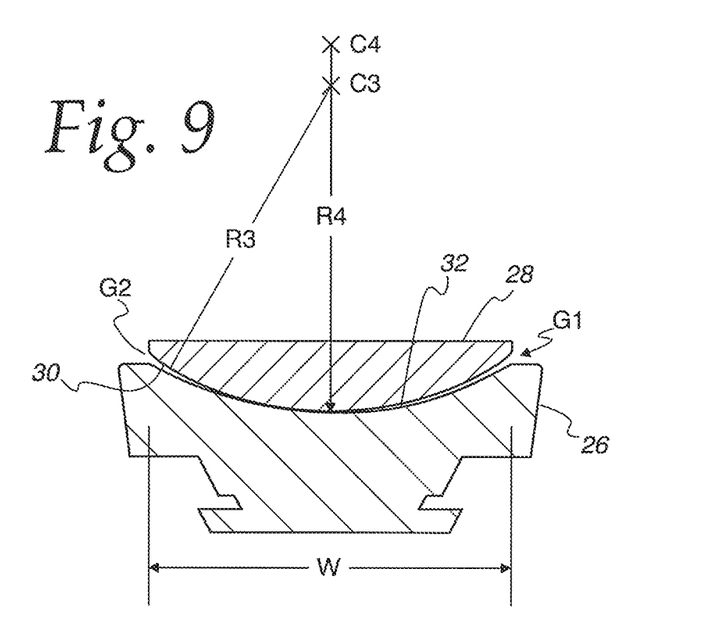
FIG. 9 is an enlarged, cross-sectional view of the prosthesis taken along line 9-9 of FIG. 7.
Figure 10:
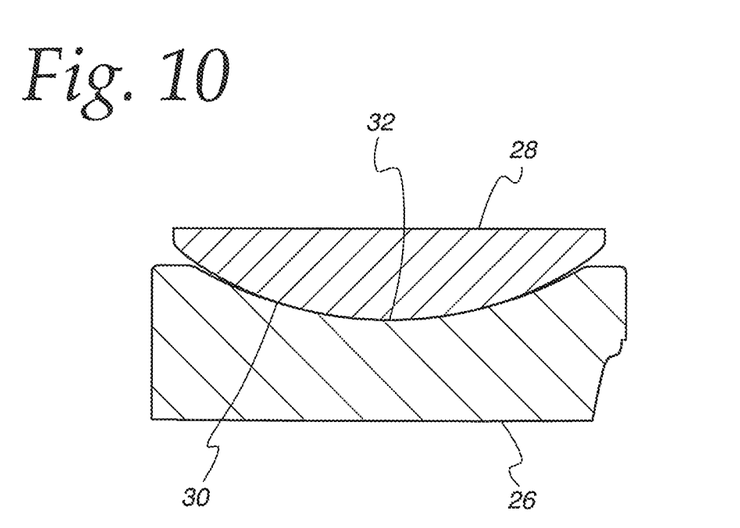
FIG. 10 is an enlarged, cross-sectional view of the prosthesis taken along line 10-10 of FIG. 7.
Figure 11:
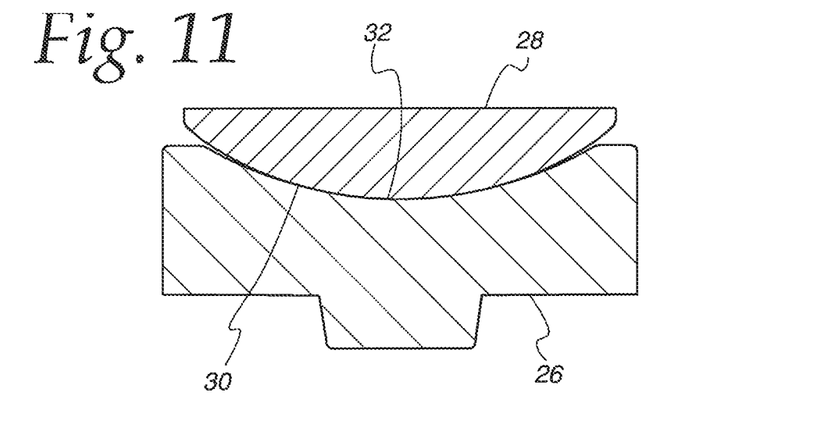
FIG. 11 is an enlarged, cross-sectional view of the prosthesis taken along line 11-11 of FIG. 7.
Figure 12:
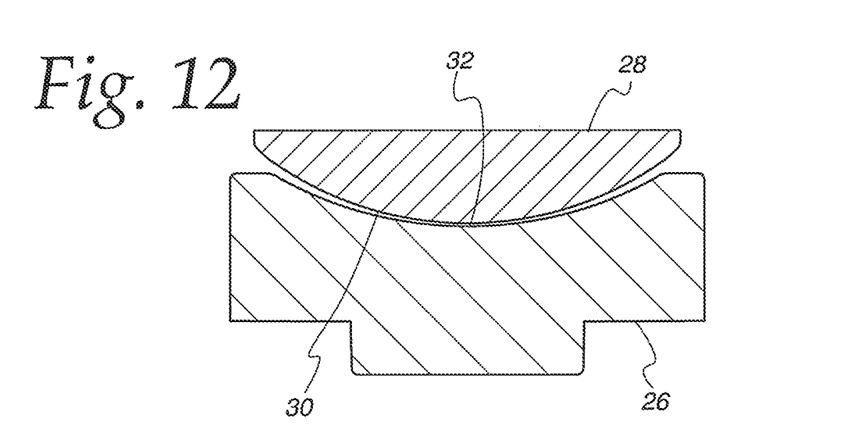
FIG. 12 is an enlarged, cross-sectional view of the prosthesis taken along line 12-12 of FIG. 7.
Figure 13:
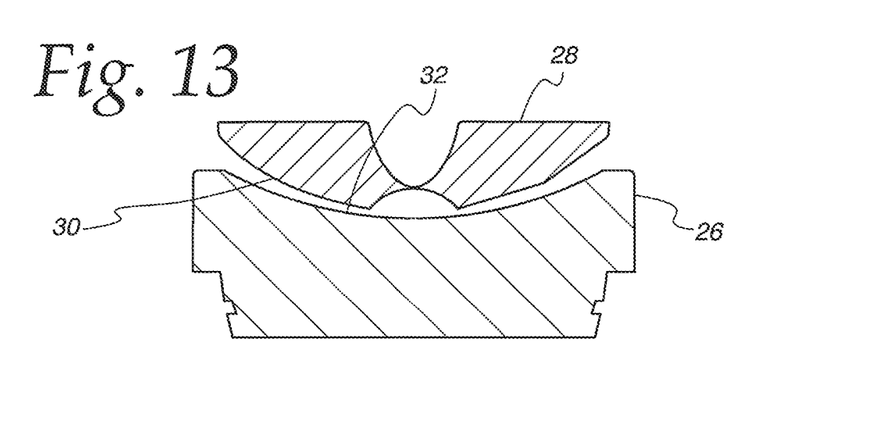
FIG. 13 is an enlarged, cross-sectional view of the prosthesis taken along line 13-13 of FIG. 7.
Figure 18:
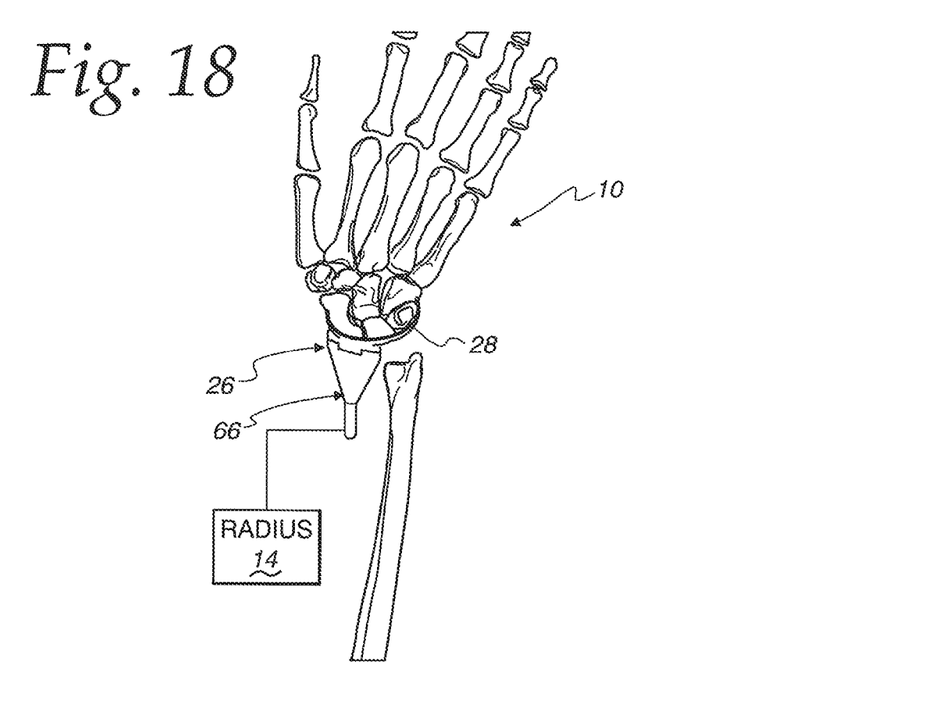
FIG. 18 is a reduced view as in FIG. 17 and showing a specific form of proximal assembly with the patient's radius removed.

The proximal assembly 26 is attached to the radius 14 using any conventional structure and technique. In FIG. 6, the proximal assembly 26 is shown connected to the radius 14 using one or more fixation parts 66 that are shown schematically in that Figure. One specific form of the fixation part(s) 66 is shown in FIG. 18.

Before the details of the configuration and interaction of the cooperating surfaces 30, 32 is described, the significance of the aforementioned manner of securement of the body 28 to the carpal bones will be described.

By transforming the separate carpal bones into a unified mass, a solid foundation is provided for the body 28. Preferably, the body 28 contacts and is stabilized by at least two of the carpal bones in the first carpal row. Ideally, all bones in the first carpal row remain intact as part of the unified mass that supports the body 28. As seen in FIG. 17, the fastener 60 extending in the line L2 is advanced in a first direction through the body 28 in the line L2 that is transverse to a reference line RL that extends generally parallel to the length of the patient's radius 14. A separate fastener 60 extending along the line L3 is advanced in a direction generally oppositely to the first direction for introduction of the fastener 60 in the line L2. The line L3 is transverse to the reference line RL. The fasteners 60 inserted in this manner are generally perpendicular to the direction of forces of distraction in the carpal region. This tends to avoid and provide resistance to distraction forces and to fractures and loosening of the fasteners 60 in the carpal region.

The surfaces 30, 32 are configured to guide relative movement between the body 28 and proximal assembly 26 in multiple dimensions. As seen in FIG. 6, the U-shaped surfaces 30, 32 are approximated by arcs of circles with radii R1, R2, respectively. The radius R1 is centered on a line C1, with the radius R2 centered on a parallel line C2. The lines C1, C2 are substantially perpendicular to a plane bisecting the patient's fingers in a flattened state with the finger lengths aligned with the length of the radius 14. The radius R1 is less than the radius R2, as a result of which the surfaces 30, 32 are not in contact over their full angular coincidence. Accordingly, the body 28 is guided by the surface 32 in an arcuate path, indicated by the double-headed arrow 68, without any substantial resistance or likelihood of binding over the angular length AL (FIG. 16) of the surface 32 that contacts the surface 30 as the hand 10 articulates relative to the radius 14.

The surfaces 30, 32 also have cooperating convex/concave shapes as viewed from a perspective taken transversely to the length L of the elongate base 42 on the body 28. This construction likewise facilitates the aforementioned guided movement of the body 28 relative to the proximal assembly 26 without significant impedance, while at the same time controlling skewing between the body 28 and proximal assembly 26.

More specifically, FIGS. 7-13 show a series of cross-sectional views from the indicated perspective over the angular range where the surfaces 30, 32 co-act. In each such view, as described with respect to representative cross-sectional view in FIG. 9, the surface 32 is approximated by an arc of a circle with a radius R4. The surface 30 is approximated by the arc of a circle with a radius R3. The radii R3, R4 are centered on spaced, parallel lines C3, C4, respectively. The radius R3 is less than the radius R4. Accordingly, there is not a conforming contact region over the full width W where the surfaces 30, 32 coincide. This has two significant advantages.

First of all, the non-conforming contact affords the necessary controlled guidance between the body 28 and proximal assembly 26 in the path indicated by the double-headed arrow 68, but does not cause any significant binding between these components.

Figure 4:
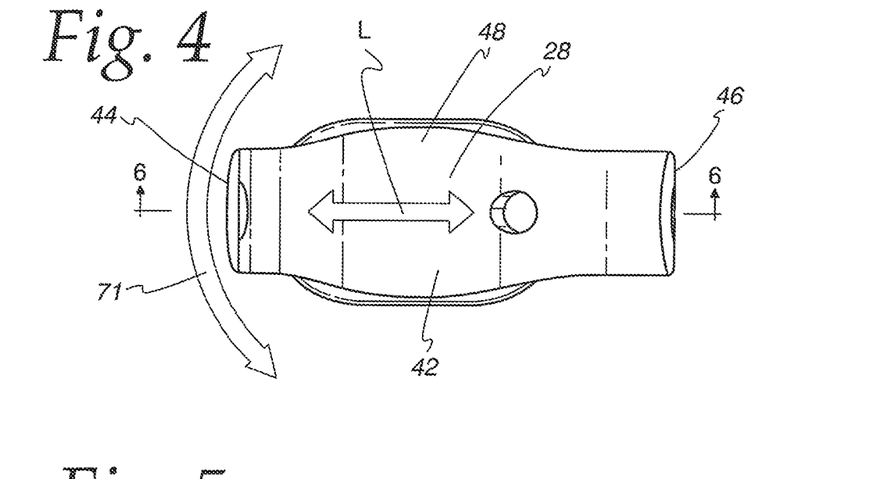
FIG. 4 is an elevation view of one particular form of the inventive prosthesis, as shown schematically in FIG. 2.
Figure 5:
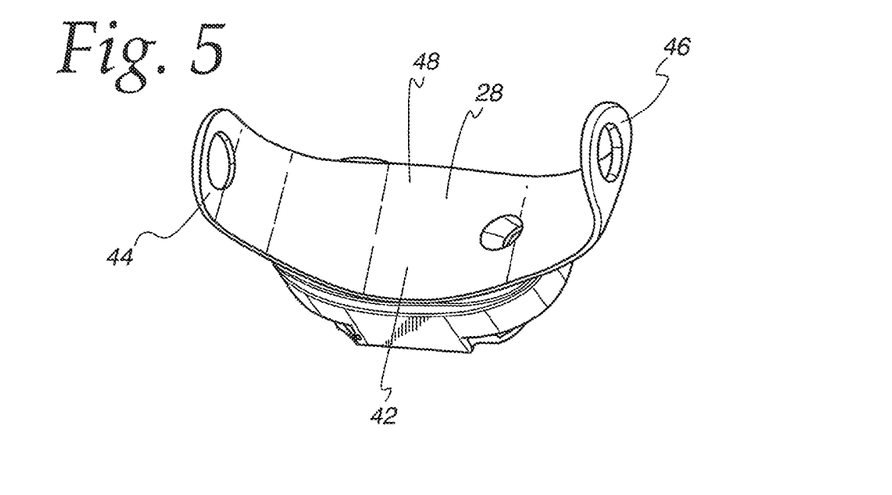
FIG. 5 is a view as in FIG. 4 from a different perspective.
Figure 19:
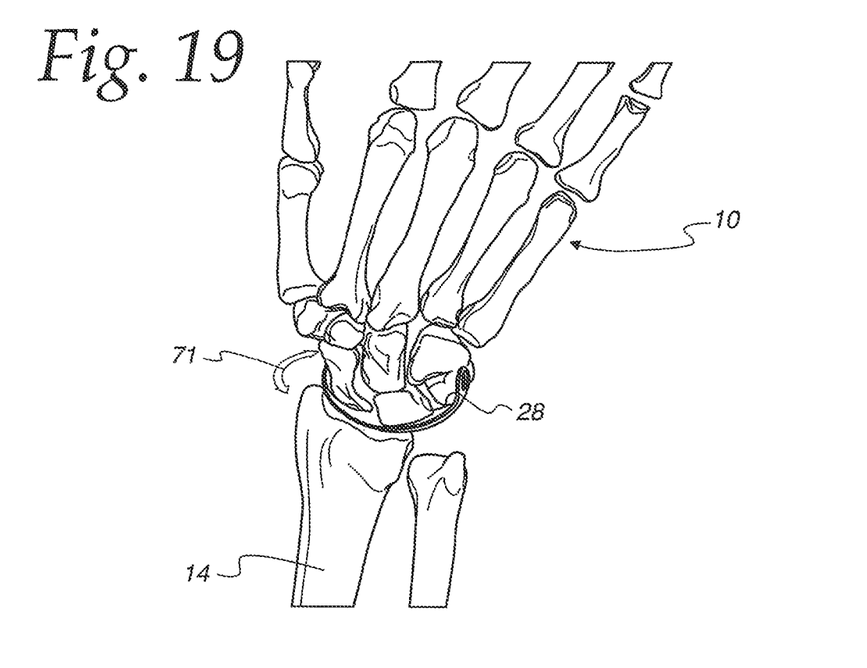
FIG. 19 is a view as in FIG. 17 with the patient's hand turned to a different orientation relative to the proximal assembly.

Secondly, the described configuration produces gaps G1, G2 between the surfaces 30, 32 at the widthwise ends of the overlapping regions of the surfaces 30, 32 region. As a result, the body 28 is allowed to turn relative to the proximal assembly 26 in a controlled range around a line 70 (FIG. 6) that extends generally parallel to the length of the patient's radius 14, as indicated by the double-headed arrow 71 (FIGS. 4 and 19). The radii R1, R2, R3, R4 can be selected to control the range of turning around the line 70, which is preferably at least 10° total, and more preferably 10°±from center. As the body 28 is turned around the line 70, the surfaces 30, 32 interfere with each other at spaced widthwise locations to block further turning.

By allowing this turning movement, an additional range of motion is allowed for the patient's hand. Further, this permitted movement may avoid breakage of the prosthesis 22 and bone fractures. Significantly, the allowed turning between the body 28 and proximal assembly 26 tends to reproduce the normal intra-carpal physiological rotation. This compensates for the normal rotation present in the carpus that is suppressed by the fusion of the carpal bones.

In this embodiment, the body has three different openings 72, 74, 76 formed therethrough at spaced locations to accept fasteners 60. Each opening 72, 74, 76 is countersunk, as previously described, to allow a head on the fasteners 60 to seat flushly with the surface 30 so as to not create a localized friction point. The opening 74 is offset closer to the leg 46 so that the fastener 60 therein is not likely to contact the surface 32 as the body 28 moves in its intended range.

The above prosthesis 22 can be inserted in post-traumatic patients and patients with osteoarthritis or chondrocalcinosis of the wrist.

As previously noted, by reason of minimal bone resection, a normal arthrodesis can be performed in the event that the prosthesis 22 fails for any reason.

The foregoing disclosure of specific embodiments is intended to be illustrative of the broad concepts comprehended by the invention.

The invention claimed is:

1. A method of reconstructing a patient's wrist to facilitate movement between the patient's hand and radius, the method comprising the steps of:
providing a prosthesis comprising proximal and distal assemblies,
wherein the distal assembly comprises a body with a U-shaped portion,
wherein the proximal and distal assemblies have surfaces that are configured to cooperate with each other to guide movement between the proximal and distal assemblies;
fixing the proximal assembly to the patient's radius;
preparing the hand for placement of the distal assembly by removing cartilage against a plurality of the patient's carpal bones without significantly altering the configuration of stable volume of at least one of the patient's carpal bones in the patient's first carpal row;
after preparing the hand for placement of the distal assembly, placing the U-shaped portion of the body against a plurality of carpal bones in the patient's first carpal row including the at least one unaltered carpal bone; and
with the U-shaped portion of the body placed against the carpal bones in the patient's first carpal row, securing separate locations on the body to a plurality of the patient's carpal bones,
the U-shaped portion of the body having a U-shaped surface that extends over a plurality of carpal bones in the patient's first carpal row, including the patient's triquetrum carpal bone.

2. The method of reconstructing a patient's wrist according to claim 1 wherein the step of removing cartilage comprises removing cartilage against the patient's scaphoid and lunate carpal bones so that the U-shaped portion of the body can be placed directly against a part of each of the scaphoid and lunate carpal bones.

3. The method of reconstructing a patient's wrist according to claim 1 wherein the U-shaped portion of the secured body extends to against each of the patient's scaphoid and lunate carpal bones.

4. The method of reconstructing a patient's wrist according to claim 1 further comprising the step of fusing a plurality of the patient's carpal bones together.

5. The method of reconstructing a patient's wrist according to claim 4 wherein the step of fusing a plurality of the patient's carpal bones together is effected through the step of securing the body to a plurality of the patient's carpal bones.

6. The method of reconstructing a patient's wrist according to claim 1 wherein the step of securing the body to a plurality of the patient's carpal bones comprises directing a plurality of fasteners into a plurality of the patient's carpal bones.

7. The method of reconstructing a patient's wrist according to claim 6 wherein the step of directing a plurality of fasteners into a plurality of the patient's carpal bones comprises directing one of the plurality of fasteners through the body and one of the patient's carpal bones and into another one of the patient's carpal bones.

8. The method of reconstructing a patient's wrist according to claim 1 wherein the body has an overall "U" shape with an elongate base having a length and extending into spaced legs, the elongate base having oppositely facing first and second U-shaped surfaces, the first U-shaped surface opening towards the patient's hand and contacting a plurality of the patient's carpal bones with the body secured to the patient's carpal bones, the "U" of the second U-shaped surface opening in the same direction as the first U-shaped surface and defining a guide surface that engages a guide surface on the proximal assembly to guide relative movement between the proximal and distal assemblies.

9. The method of reconstructing a patient's wrist according to claim 8 wherein the body is made as a single piece.

10. The method of reconstructing a patient's wrist according to claim 8 wherein a spacing between fingertips on the patient's hand and the second U-shaped surface is substantially the same as a dimension of the patient's hand between the fingertips and radius before the patient's hand is prepared for placement of the distal assembly and without the prosthesis.

11. The method of reconstructing a patient's wrist according to claim 8 wherein the guide surface on the body is convex in shape with the body viewed from a cross-sectional perspective taken transversely to the length of the elongate base and the guide surface on the proximal assembly is concave in shape and complementary to the convex shape on the body as viewed in cross section corresponding to the cross-sectional perspective for the body.

12. The method of reconstructing a patient's wrist according to claim 11 wherein the convex and concave shapes are approximated by arcs of circles with first and second radii respectively and the second radius is greater than the first radius.

13. The method of reconstructing a patient's wrist according to claim 1 wherein the step of providing a prosthesis comprises providing a prosthesis wherein the proximal and distal assemblies are configured to guide relative movement of the patient's hand relative to the patient's radius about a line that extends generally parallel to a length of the patient's radius.

14. The method of reconstructing a patient's wrist according to claim 13 wherein the proximal and distal assemblies are configured to guide relative movement of the patient's hand relative to the patient's radius around the line through a controlled range on the order of at least 20°.

15. The method of reconstructing a patient's wrist according to claim 1 wherein the proximal and distal assemblies have control surfaces that abut to limit relative turning of the distal assembly in opposite directions relative to the proximal assembly around a line that extends generally parallel to a length of the patient's radius, the control surfaces configured so that the distal assembly can turn around the line relative to the proximal assembly through a range of at least 10°.

16. The method of reconstructing a patient's wrist according to claim 1 wherein the body has an overall "U" shape with a U-shaped surface, engaging a U-shaped surface on the proximal assembly, the U-shaped surfaces each approximated by an arc with a radius centered on a line substantially perpendicular to a plane bisecting the patient's fingers in a flattened state, wherein the radius of the arc approximating the U-shaped surface on the proximal assembly is greater than the radius of the arc approximating the U-shaped surface on the body.

17. A method of reconstructing a patient's wrist to facilitate movement between the patient's hand and radius, the method comprising the steps of;
   providing a prosthesis comprising proximal and distal assemblies,
   wherein the distal assembly comprises a body with a U-shaped portion,
   wherein the proximal and distal assemblies have surfaces that are configured to cooperate with each other to guide movement between the proximal and distal assemblies;
   fixing the proximal assembly to the patient's radius;
   preparing the hand for placement of the distal assembly by removing cartilage against a plurality of the patient's carpal bones without significantly altering the configuration of stable volume of at least one of the patient's carpal bones in the patient's first carpal row;
   after preparing the hand for placement of the distal assembly, placing the U-shaped portion of the body against a plurality of carpal bones in the patient's first carpal row including the at least one unaltered carpal bone; and
   with the U-shaped portion of the body placed against the carpal bones in the patient's first carpal row, securing separate locations on the body to a plurality of the patient's carpal bones,
   wherein the step of removing cartilage comprises removing cartilage from between the patient's lunate carpal bone and each of the scaphoid and capitate carpal bones.

18. A method of reconstructing a patient's wrist to facilitate movement between the patient's hand and radius, the method comprising the step of:
   providing a prosthesis comprising proximal and distal assemblies,
   wherein the distal assembly comprises a body with a U-shaped portion,
   wherein the proximal and distal assemblies have surfaces that are configured to cooperate with each other to guide movement between the proximal and distal assemblies;
   fixing the proximal assembly to the patient's radius;
   preparing the hand for placement of the distal assembly by removing cartilage against a plurality of the patient's carpal bones without significantly altering the configuration of stable volume of at least one of the patient's carpal bones in the patient's first carpal row;
   after preparing the hand for placement of the distal assembly, placing the U-shaped portion of the body against a plurality of carpal bones in the patient's first carpal row including the at least one unaltered carpal bone; and
   with the U-shaped portion of the body placed against the carpal bones in the patient's first carpal row, securing separate locations on the body to a plurality of the patient's carpal bones,
   wherein the U-shaped portion of the secured body extends to against the patient's triquetrum carpal bone,
   wherein the step of removing cartilage comprises removing cartilage against the triquetrum carpal bone so that the U-shaped portion of the body can be placed directly against a part of the triquetrum carpal bone.

19. The method of reconstructing a patient's wrist according to claim 18 wherein the step of removing cartilage comprises removing cartilage from between the triquetrum carpal bone and the patient's hamate carpal bone.

20. A method of reconstructing a patient's wrist to facilitate movement between the patient's hand and radius, the method comprising the steps of:
providing a prosthesis comprising proximal and distal assemblies,
wherein the distal assembly comprises a body with a U-shaped portion,
wherein the proximal and distal assemblies have surfaces that are configured to cooperate with each other to guide movement between the proximal and distal assemblies;
fixing the proximal assembly to patient's radius;
preparing the hand for placement of the distal assembly by removing cartilage against a plurality of the patient's carpal bones without significantly altering the configuration of stable volume of at least one of the patient's carpal bones in the patient's first carpal row:
after preparing the hand for placement of the distal assembly, placing the U-shaped portion of the body against a plurality of carpal bones in the patient's first carpal row including the at least one unaltered carpal bone; and
with the U-shaped portion of the body placed against the carpal bones in the patient's first carpal row, securing separate locations on the body to a plurality of the patient's carpal bones,
wherein the step of securing the body to a plurality of the patient's carpal bones comprises directing a plurality of fasteners into a plurality of the patient's carpal bones,
wherein the step of directing a plurality of fasteners into a plurality of the patient's carpal bones comprises directing: a) a first fastener in a first direction through the body and into one of the patient's carpal bones along a first line that is transverse to a reference line that extends generally parallel to a length of the patient's radius; and b) a second fastener in a second direction through the body and into one of the patient's carpal bones along a second line that is transverse to the reference line, the first and second directions being generally opposite to each other.

21. The method of reconstructing a patient's wrist according to claim 20 wherein the first fastener is directed through the patient's triquetrum carpal bone and into the patient's hamate carpal bone.

22. A method of reconstructing a patient's wrist to facilitate movement between the patient's hand and radius, the method comprising the steps of:
providing a prosthesis comprising proximal and distal assemblies,
wherein the distal assembly comprises a body with a U-shaped portion,
wherein the proximal and distal assemblies have surfaces that are configured to cooperate with each other to guide movement between the proximal and distal assemblies;
fixing the proximal assembly to the patient's radius;
preparing the hand for placement of the distal assembly by removing cartilage against a plurality of the patient's carpal bones without significantly altering the configuration of stable volume of at least one of the patient's carpal bones in the patient's first carpal row;
after preparing the hand for placement of the distal assembly, placing the U-shaped portion of the body against a plurality of carpal bones in the patient's first carpal row; and
with the U-shaped portion of the body placed against the carpal bones in the patient's first carpal row, securing separate locations on the body to a plurality of the patient's carpal bones,
wherein the step of securing the body to a plurality of the patient's carpal bones comprises directing a plurality of fasteners into a plurality of the patient's carpal bones,
wherein the step of directing a plurality of fasteners into a plurality of the patient's carpal bones comprises directing: a) a first fastener in a first direction through the body and into one of the patient's carpal bones along a first line that is transverse to a reference line that extends generally parallel to a length of the patient's radius; and b) a second fastener in a second direction through the body and into one of the patient's carpal bones along a second line that is transverse to the reference line, the first and second directions being generally opposite to each other,
wherein the first fastener is directed through the patient's triquetrum carpal bone and into the patient's hamate carpal bone,
wherein the second fastener is directed through the patient's scaphoid carpal bone and into the patient's capitate carpal bone.

23. A method of reconstructing a patient's wrist to facilitate movement between the patient's hand and radius, the method comprising the steps of:
providing a prosthesis comprising proximal and distal assemblies,
wherein the distal assembly comprises a body with a U-shaped portion,
wherein the proximal and distal assemblies have surfaces that are configured to cooperate with each other to guide movement between the proximal and distal assemblies;
fixing the proximal assembly to the patient's radius;
preparing the hand for placement of the distal assembly by removing cartilage against a plurality of the patient's carpal bones without significantly altering the configuration of stable volume of at least one of the patient's carpal bones in the patient's first carpal row;
after preparing the hand for placement of the distal assembly, placing the U-shaped portion of the body against a plurality of carpal bones in the patient's first carpal row; and
with the U-shaped portion of the body placed against the carpal bones in the patient's first carpal row, securing separate locations on the body to a plurality of the patient's carpal bones,
wherein the body has an overall "U" shape with an elongate base having a length and extending into spaced legs, the elongate base having oppositely facing first and second U-shaped surfaces, the first U-shaped surface opening towards the patient's hand and contacting a plurality of the patient's carpal bones with the body secured to the patient's carpal bones, the "U" of the second U-shaped surface opening in the same direction as the first U-shaped surface and defining a guide surface that engages a guide surface on the proximal assembly to guide relative movement between the proximal and distal assemblies, wherein the body has an opening in the base and an opening in each of the spaced legs each to accept a fastener, the legs extending in substantially parallel relationship to each other.

24. A method of reconstructing a patient's wrist to facilitate movement between the patient's hand and radius, the method comprising the steps of:
providing a prosthesis comprising proximal and distal assemblies,
wherein the distal assembly comprises a body with a U-shaped portion,
wherein the proximal and distal assemblies have surfaces that are configured to cooperate with each other to guide movement between the proximal and distal assemblies;
fixing the proximal assembly to the patient's radius;
preparing the hand for placement of the distal assembly by removing cartilage against a plurality of the patient's carpal bones without significantly altering the configuration of stable volume of at least one of the patient's carpal bones in the patient's first carpal row;
after preparing the hand for placement of the distal assembly, placing the U-shaped portion of the body against a plurality of carpal bones in the patient's first carpal row including the at least one unaltered carpal bone; and
with the U-shaped portion of the body placed against the carpal bones in the patient's first carpal row, securing separate locations on the body to a plurality of the patient's carpal bones.
wherein the step of securing separate locations on the body to a plurality of the patient's carpal bones comprises using a plurality of separate fasteners directed into the carpal bones at the separate locations that are spaced from each other on the body to secure the separate locations on the body to a plurality of the patient's carpal bones.

* * * * *